United States Patent
Tai et al.

(10) Patent No.: US 7,774,931 B2
(45) Date of Patent: Aug. 17, 2010

(54) METHOD OF FABRICATING AN INTEGRATED INTRAOCULAR RETINAL PROSTHESIS DEVICE

(75) Inventors: Yu-Chong Tai, Pasadena, CA (US); Damien C. Rodger, South Pasadena, CA (US); Wen Li, East Lansing, CA (US); Mark Humayun, Glendale, CA (US); James D. Weiland, Valencia, CA (US); Hossein Ameri, Galveston, TX (US); Armand R. Tanguay, Jr., Yorba Linda, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 673 days.

(21) Appl. No.: 11/414,139

(22) Filed: Apr. 28, 2006

(65) Prior Publication Data

US 2006/0282128 A1    Dec. 14, 2006

Related U.S. Application Data

(60) Provisional application No. 60/675,645, filed on Apr. 28, 2005, provisional application No. 60/790,666, filed on Apr. 10, 2006.

(51) Int. Cl.
    *H05K 3/30*    (2006.01)
(52) U.S. Cl. .......................... 29/832; 29/592.1; 29/831; 29/847; 29/885; 607/53; 607/116; 607/141
(58) Field of Classification Search ................ 29/592.1, 29/831, 832, 847, 885; 607/53, 116, 141
    See application file for complete search history.

(56) References Cited

U.S. PATENT DOCUMENTS 5,306,670 A * 4/1994 Mowatt et al. ................. 29/832

(Continued)

FOREIGN PATENT DOCUMENTS

WO    WO 2004/014479 A2    2/2004

(Continued)

OTHER PUBLICATIONS

Banks, R.H. "Laser Generated Conductive Lines," *IBM Technical Disclosure Bulletin*, Aug. 1976, vol. 19, No. 3, p. 1014.

(Continued)

*Primary Examiner*—Paul D Kim
(74) *Attorney, Agent, or Firm*—Townsend and Townsend and Crew LLP; Gerald T. Gray

(57) ABSTRACT

Intraocular retinal prosthesis devices and methods for fabricating the same. A prosthesis device includes a cable region that connects an electrode array region with a power and data management region. The electrode array region includes one or more arrays of exposed electrodes, and the power and data management region includes various power and control elements. The power and data management elements, in one aspect, include an RF coil or coils and circuit arrangements and/or chips configured to provide drive signals to the electrodes via a cable and receive power and signals from the RF coil or coils. Each region includes elements fabricated on or in a single polymer layer during the same fabrication process.

16 Claims, 12 Drawing Sheets

U.S. PATENT DOCUMENTS

| | | |
|---|---|---|
| 5,471,073 A | 11/1995 | Kohno |
| 5,735,721 A | 4/1998 | Choi |
| 5,749,997 A * | 5/1998 | Tang et al. .................. 156/249 |
| 6,324,429 B1 | 11/2001 | Shire et al. |
| 7,326,649 B2 | 2/2008 | Rodger et al. |
| 2002/0198573 A1 | 12/2002 | Nisch et al. |
| 2003/0158588 A1 | 8/2003 | Rizzo et al. |
| 2003/0187491 A1 | 10/2003 | Greenberg et al. |

FOREIGN PATENT DOCUMENTS

| | | |
|---|---|---|
| WO | WO 2004/014479 A3 | 2/2004 |
| WO | WO 2006/116625 A2 | 11/2006 |

OTHER PUBLICATIONS

Curcio, C.A. et al., "Topography of Ganglion-Cells in Human Retina," *The Journal of Comparative Neurology*, 1990, vol. 300, pp. 5-25.

International Search Report mailed on Jul. 7, 2008, for PCT Application No. PCT/US06/16070 filed on Apr. 28, 2006, 4 pages.

* cited by examiner

Parlene N

Parlene C

Parlene D

METHOD OF FABRICATING AN INTEGRATED INTRAOCULAR RETINAL PROSTHESIS DEVICE

CROSS-REFERENCES TO RELATED APPLICATIONS

This application claims the benefit of U.S. Provisional Application No. 60/675,645, filed Apr. 28, 2005, and 60/790,666, titled "Retinotopic Layout for Retinal Prosthesis" filed Apr. 10, 2006, the disclosures of which are each incorporated herein by reference in its entirety.

STATEMENT AS TO RIGHTS TO INVENTIONS MADE UNDER FEDERALLY SPONSORED RESEARCH OR DEVELOPMENT

The government may have certain rights to the invention based on National Science Foundation Grant EEC-0310723.

BACKGROUND OF THE INVENTION

The present invention relates generally to retinal prosthesis devices, and more particularly to integrated retinal prosthesis devices and methods of manufacturing one or multiple such devices in monolithic processes.

Intraocular retinal prostheses typically can be considered to comprise three separate subsystems. One subsystem typically includes a radiofrequency coil for power and data transmission and recovery to an externally placed coil. A second subsystem typically includes a multielectrode array for retinal stimulation. The third subsystem typically includes an integrated circuit or discrete components for power recovery and data decoding with analog and/or digital circuitry for driving the electrode array. FIG. 1 shows and example of such a prosthesis and its component subsystems.

However, these three components are fabricated as separate components and combined to form the prosthesis system. This typically requires multiple fabrication processes, e.g., one for each device component, in addition to a process for interconnecting and coupling the various components together to form the prosthesis system. Such an overall system fabrication process can be overly complex and time consuming and inefficient. Additionally, the electrode arrays do not take into consideration the topology of the target retinal cells to be stimulated.

Therefore it is desirable to provide systems and methods that overcome the above and other problems. In particular, it is desirable to provide systems and methods that are fast and reliable and which allow for multiple system components to be fabricated in a monolithic fabrication process. It is further desirable that such systems include electrode arrays that are optimized for enhanced retinal stimulation.

BRIEF SUMMARY OF THE INVENTION

The present invention provides intraocular retinal prosthesis systems and methods for fabricating the same. In one aspect, fabrication of all or multiple components of a prosthesis device or system are combined into a single monolithic fabrication process. Also, many such entire systems can be fabricated simultaneously in a single microfabrication processing run. Additionally, the geometries of a batch-fabricated device are considered in order for the system to be implantable and functional within the intraocular space.

A device according to the present invention includes a cable region that connects an electrode array region with a power and data management region. The electrode array region includes one or more arrays of exposed electrodes, and the power and data management region includes various power and control elements. For example, the power and data management elements, in one aspect, include an RF coil or coils and circuit arrangements and/or chips configured to provide drive signals to the electrodes via a cable and receive power and signals from the RF coil or coils. Each region includes elements fabricated on a polymer layer during the same fabrication process.

Advantageously, the present invention provides a system that combines all components in a single, integrated intraocularly-implantable device. In certain aspects, the components of the device structure have optimized geometries that enable implantation and enhanced functionality of the complete system, and have determined optimal subsystem locations within the eye. This mechanical design has been demonstrated using parylene as the bulk substrate, but can be fabricated using different materials and in many alternative geometries. In one aspect, the portion of the device to be implanted in the lens capsular bag is configured with retention elements that anchor that portion in the lens capsular bag and decreases traction or pulling of the device in this region into the vitreous cavity, e.g., due to the cable (cabling effect).

In one aspect, an electrode array is provided that has an exposed electrode pattern density configured to match the topology of the target cells to be stimulated, e.g., ganglion cells of the retina.

According to one aspect of the present invention, a method is provided for fabricating an integrated intraocular retinal prosthesis device having an electrode array region, a power and data management region and a cable region connecting the electrode region with the power and data management region. The method typically includes forming a patterned layer of conductive material on a first layer of polymer material, the patterned conductive layer defining circuit elements of the power and data management region, the electrode region and the cable region, and covering the patterned conductive layer with a second polymer layer. The method also typically includes removing a portion of the second polymer layer in the electrode array region so as to expose at least a portion of the patterned conductive layer to form an exposed electrode array. In certain aspects, the first polymer layer and the second polymer layer each include one or more of parylene A, parylene C, parylene AM, parylene F, parylene N, parylene HT or parylene D. In certain aspects, the conductive material includes one or more of carbonized parylene, gold, platinum, chromium, titanium, platinum and iridium oxide. In certain aspects, the circuit elements include one or more RF coils. In certain aspects, the device includes one or more retention elements configured to retain at least a portion of the circuit elements in an implant region of an eye. In certain aspects, the exposed electrode array includes electrodes arranged in a pattern having an irregular density and/or a density pattern that mimics the pattern of ganglion cells in a retina.

According to another aspect of the present invention, an integrated intraocular retinal prosthesis device formed on a layer of polymer material is provided. The device typically includes a first region including a plurality of electrodes, a second region including one or more RF coils and a plurality of control circuit elements coupled with the one or more RF coils. The device also typically includes a third region including an interconnect medium having one or more conductive lines that couple the electrodes with the plurality of control circuit elements, wherein the control circuit elements and each of the three regions are fabricated on or in the same polymer layer. In certain aspects, the polymer layer includes one or more of parylene A, parylene C, parylene AM, parylene F, parylene N, parylene HT or parylene D. In certain aspects, the conductive lines includes one or more of carbonized parylene, gold, platinum, chromium, titanium, platinum and iridium oxide. In certain aspects, the exposed portions of the electrodes are arranged in a pattern having an irregular density and/or a density pattern that mimics the pattern of ganglion cells in a retina.

According to yet another aspect, the present invention provides an integrated prosthesis device implanted in an eye wherein the first region is located proximal to the retina, and wherein the second region is located within or proximal to a capsular bag region of the eye. In certain aspects, the device includes one or more retention elements configured to retain the RF coils in an implant region of an eye. In certain aspects, control circuit elements are included in the second region.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides intraocular prosthesis systems and devices and methods of manufacturing the same. In one embodiment, all or a portion of the components of an intraocular prosthesis system or device are fabricated in a monolithic fabrication process. Additionally, multiple systems can be fabricated in a single batch fabrication process.

A prosthesis device according to one embodiment of the invention includes a power and data management subsystem, a retinal stimulation subsystem and an interconnect medium for providing signals between the power and data management subsystem and the retinal stimulation subsystem. In one aspect, the power and data management subsystem includes one or several radio-frequency (RF) coils and one or several intelligence modules, e.g., circuit arrangements or packaged chips. The stimulation subsystem includes one or several multielectrode array regions. In certain aspects, a multielectrode array includes electrodes arranged with a density pattern that is optimized to stimulate the ganglion cells in the retina. One or several connection cables interconnect the electrode arrays with the intelligence module(s) to allow for control of an electrode array by an intelligence module.

A device according to one aspect is fabricated using one or several polymers as the bulk substrate material, although substrate materials such as silicon, glass, etc may be used as a platform for device formation. A metal and/or a conductive polymer and/or other conductive materials form the connection lines embedded within the cables and other device regions. The final geometry of the system is formed in the polymer material, e.g., etched using oxygen plasma or other techniques (e.g. excimer laser, blade) and where a substrate/platform is used for fabrication, the device is removed from the substrate.

Figure 1:
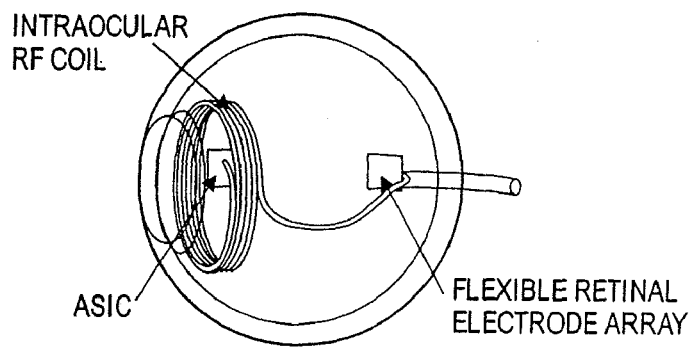
FIG. 1 illustrates a typical intraocular retinal prosthesis system and the approximate locations of the system components when implanted in an eye.
Figure 2:
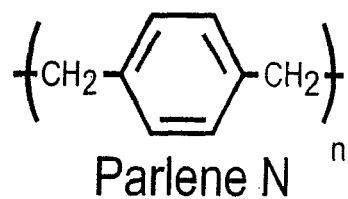
FIG. 2 illustrates the chemical structures of the three most common parylenes.
Figure 2:
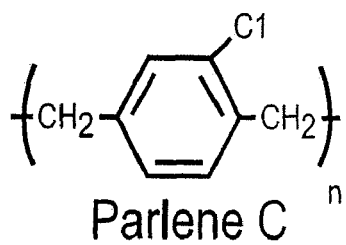
Figure 2:
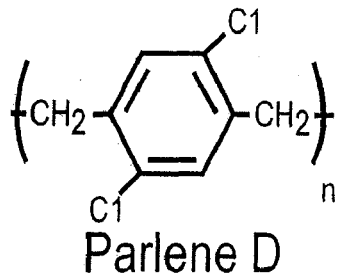

In certain aspects, parylene is used as the base material for device fabrication due, in part, to its proven biocompatibility and its ease of integration with standard microfabrication processes and techniques. Parylene is a USP Class VI biocompatible polymer that can be deposited through a highly-conformal vapor deposition process. Types of parylene include parylene C, F, A, AM, N, D and HT. Of the three most common types of parylene, shown in FIG. 2, parylene C is perhaps the most widely used in industry. The advantages of the use of parylene include its proven biocompatibility, its strength and flexibility (e.g., Young's modulus ≈4 GPa), its conformal pinhole-free room-temperature deposition, its low dielectric constant (≈3) and high volume resistivity (>$10^{16}$ Ω-cm), its transparency, and its ease of manipulation using standard microfabrication techniques such as reactive ion etching (RIE). Several research groups have used parylene C deposition as a method of creating a biocompatible, water-blocking seal around electrode arrays typically fabricated using a polyimide substrate. This is necessary because most polyimides have a moisture absorption that is more than an order of magnitude higher than that of parylene C. Some specialized polyimide films have lower moisture absorption, but they require high-temperature curing steps that are generally not post-IC compatible, and their use in permanent medical implants is not permitted.

Figure 3:
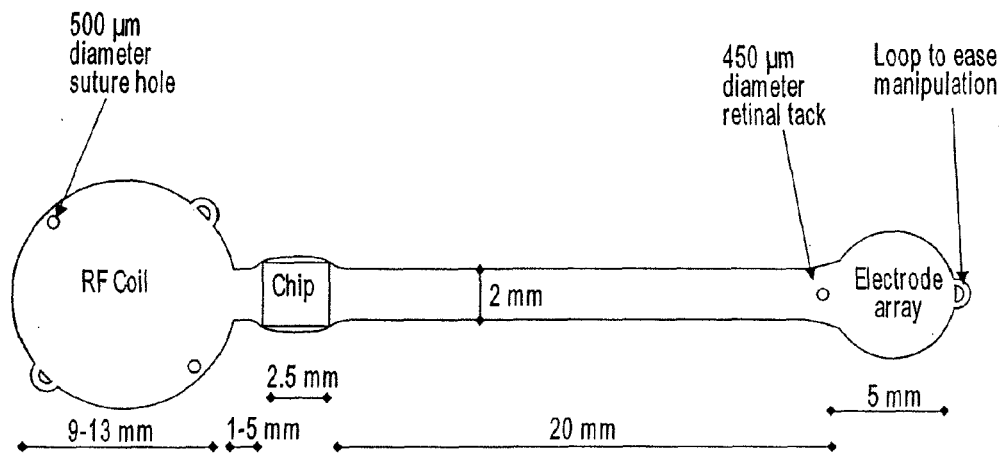
FIG. 3 illustrates an example of a prosthesis device according to one embodiment of the present invention.

FIG. 3 illustrates a prosthesis device 10 according to one embodiment. As shown, device 10 includes a retinal stimulation subsystem 20 including one or more electrode arrays and a power and data management subsystem 30, including one or several RF coils 32 and one or several intelligence modules 34. An interconnect medium 40 couples the retinal stimulation subsystem 20 with the intelligence modules 34. As shown in FIG. 3, the various subsystems and components of device 10 are marked, and may be referred to hereafter, as "RF Coil", "chip", "cable" and "electrode array".

Figure 21:
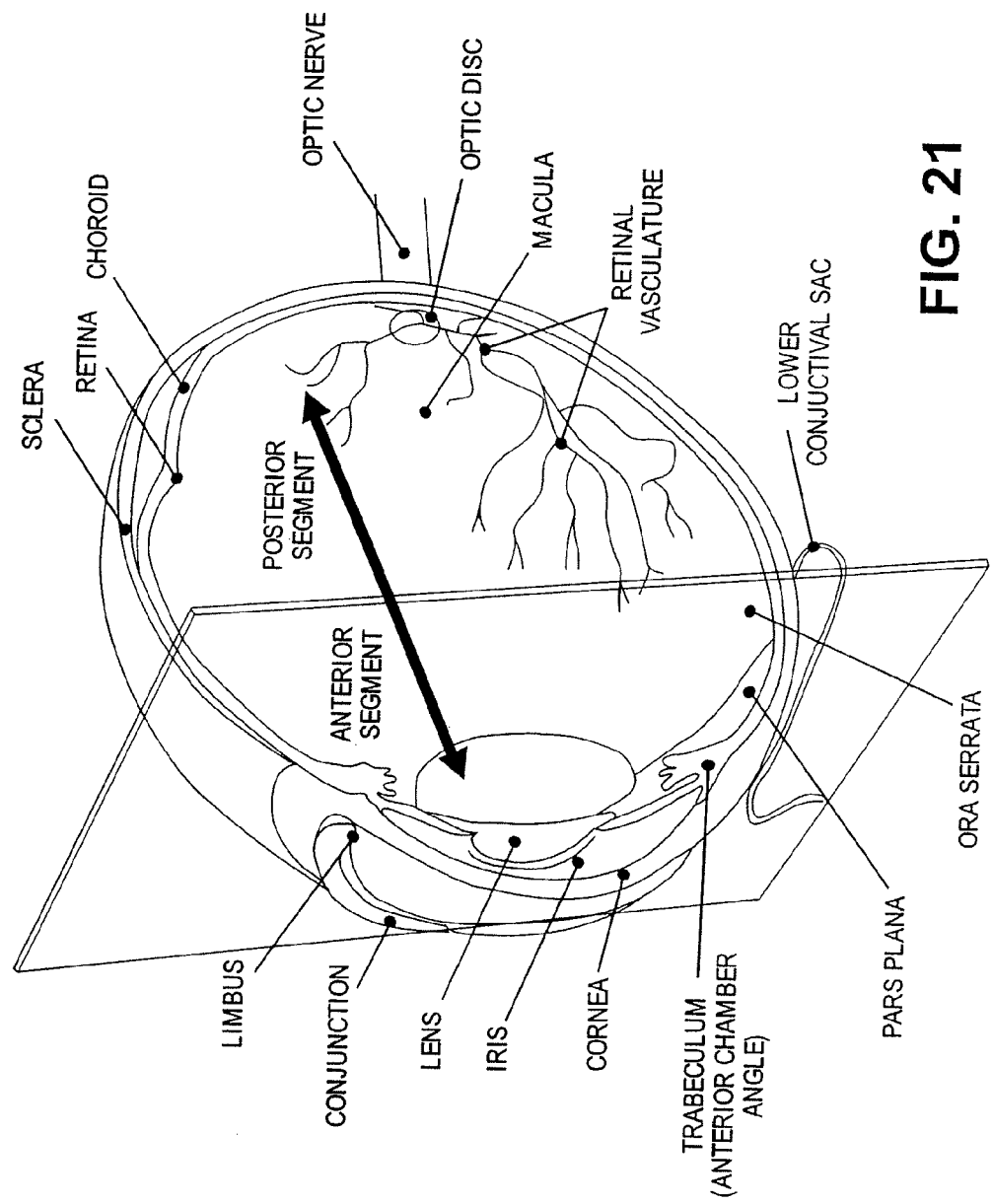
FIG. 21 illustrates the anatomy of an eye as a reference.

In one aspect, subsystem 30 includes a polymer-based RF coil having one or several layers of conducting lines embedded therein. The coil is designed, in one aspect, to be placed in the capsular bag (region of crystalline lens with lens removed) or in the sulcus just anterior to this region. In one aspect, optional suture loops or holes are provided so that the device can be sutured or fastened to the capsule, ciliary body, or sclera. See, e.g., FIG. 21 for a view of the anatomy of an eye. In one aspect, the approximate diameter of the RF coil outline is between about 9 mm and about 13 mm. However, the diameter can be smaller or larger and the precise topology and morphology of the RF coil region (and the optional suture holes or loops) can be varied according to the specific implementation. According to one aspect, the regions to the right of the RF coil region in FIG. 3 are designed to be threaded through a surgically-defined incision in the posterior capsule into the vitreous cavity (see FIG. 21 for eye anatomy; the region posterior to the lens in the posterior segment is the vitreous cavity).

Subsystem 30 also includes one or more circuit arrangements or chips 34. The chip(s) is/are responsible for power and data recovery from the RF coil, and driving of the individual electrodes on the electrode array. In certain aspects, for example, a circuit arrangement or chip includes elements for receiving and storing electrical energy and delivering the electrical energy to various system components, elements for storing data and providing control signals to an electrode array and elements for receiving signals and/or energy from an RF coil. In certain aspects, as shown in FIG. 3, a chip 34 is located on cable 40 proximal the RF coil region. However, a chip may be located elsewhere in the device. For example, a chip may be located within the RF coil region and contained within the capsular bag when implanted (see, e.g., FIG. 15), or a chip can be located closer to the electrode array region. In one aspect, one or more chips are electrically connected to both the RF coil and electrode array region using one or a plurality of conductive lines fabricated of metal, conductive polymer or other conductive materials. In certain aspects, defined regions, e.g., interconnect holes, in the polymer are provided to expose portions of the conductive materials. The interconnect holes can be defined during device fabrication using oxygen plasma etching (masked by photoresist) or excimer laser ablation, or other techniques. The chip region(s) are ideally encased and/or embedded within polymers or a metallic package, but other packaging materials and technologies can be used. The precise geometry/geometries of the chip region(s) can be varied, however, in certain aspects it is desirable that each chip does not exceed approximately 10 mm×10 mm to facilitate implantation.

In certain aspects, the cable 40 includes one or more conductive lines embedded within one or several layers of the cable polymer. The cable connects the chip(s) to the electrode array region. In one aspect, to facilitate implantation in an eye, the total length of the cable region is about 10 mm to about 20 mm, and the width is about 1.0 mm to about 10 mm. The width can be varied because the cable is foldable or rollable so as to fit through the posterior capsule incision upon implantation.

Stimulation subsystem 20, in certain aspects, includes one or more electrode arrays. In one aspect, the electrode array is circular as shown, having a diameter of between about 1 mm and about 10 mm (1 cm) in diameter. However, the array does not have to be circular in nature as shown in FIG. 3, but can be of any reasonable shape such as square or rectangular (see, e.g., FIG. 11), and of any reasonable size depending upon the desired application. To facilitate implantation in an eye, for example, the electrode array should be approximately 5 mm in diameter, but can be smaller or larger depending on the specific implementation (because this region is foldable/rollable, it can fit through small incisions). The electrodes within the array are exposed by oxygen plasma etching or excimer laser ablation, or some other method during device fabrication. As shown, an optional retinal tack region is provided for insertion of a retinal tack for connection of the array to the retina. The location and geometry of the tack region can be varied. Also as shown, an optional loop is provided for facilitating surgical manipulation, however other techniques can be used to facilitate surgical implantation (e.g. post, hole for forceps, etc.). In certain aspects, an electrode array (and other polymer fabricated elements) can be heat formed to match curvatures of the eye to facilitate implantation.

Figure 4:
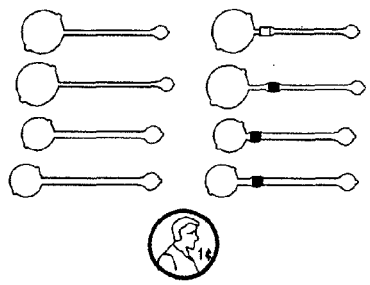
FIG. 4 illustrates examples of fabricated or partially fabricated prosthesis devices in comparison with a penny.
Figure 5:
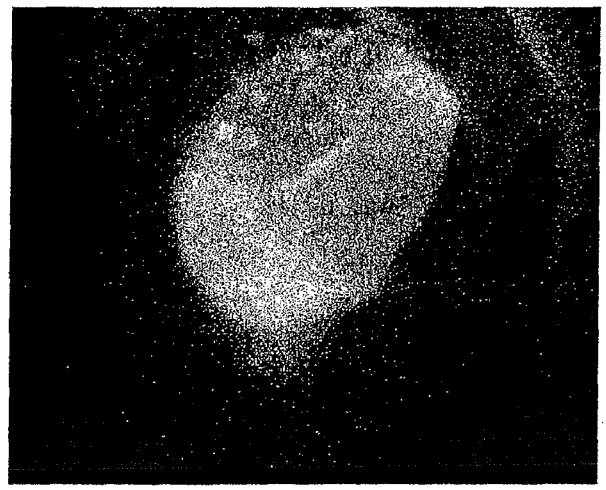
FIG. 5 illustrates an example of a prosthesis device implanted in an enucleated pig's eye.

In certain aspects, when parylene (e.g., parylene C) is used as the base device material, it is desired that each region or subsystem of the device have a thickness of between about 5 µm and about 30 µm (the thicknesses from region to region do not have to be the same), although thicker layers may be used. Regions of the device can be heat-formed or molded to specifically match the curvature of various aspects of the eye. Examples of devices fabricated according to one embodiment (but without conductive lines) are shown in FIG. 4. As shown in FIG. 5, these devices have since been implanted in enucleated pig eyes as a surgical demonstration.

Figure 6:
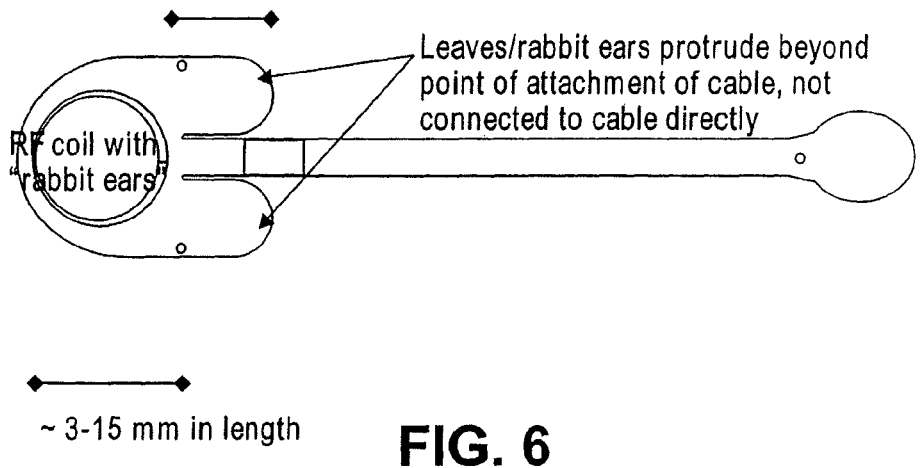
FIG. 6 illustrates an overhead depiction and approximate geometry and sizes of a prosthesis device including an RF coil with "ear" shaped retention elements.
Figure 7:
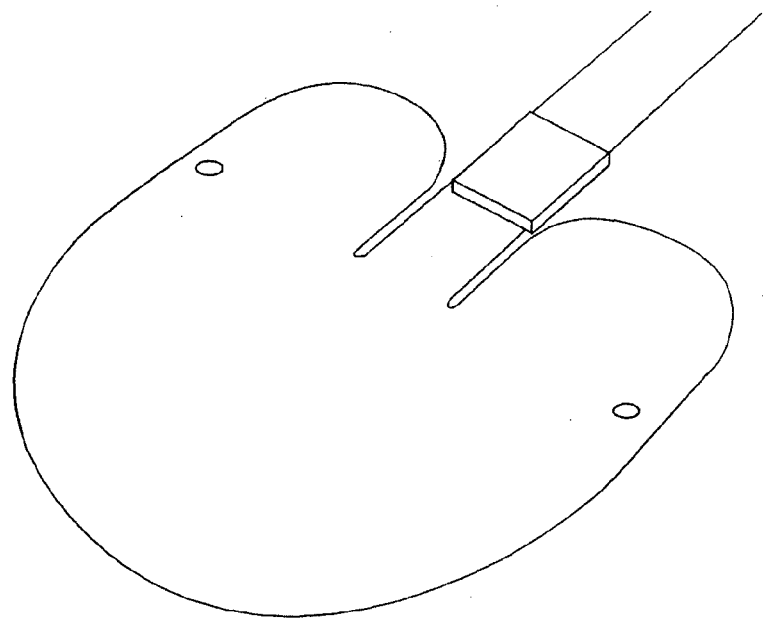
FIG. 7 illustrates an angled view of a prosthesis device including an RF coil with leaves/rabbit ears.
Figure 8:
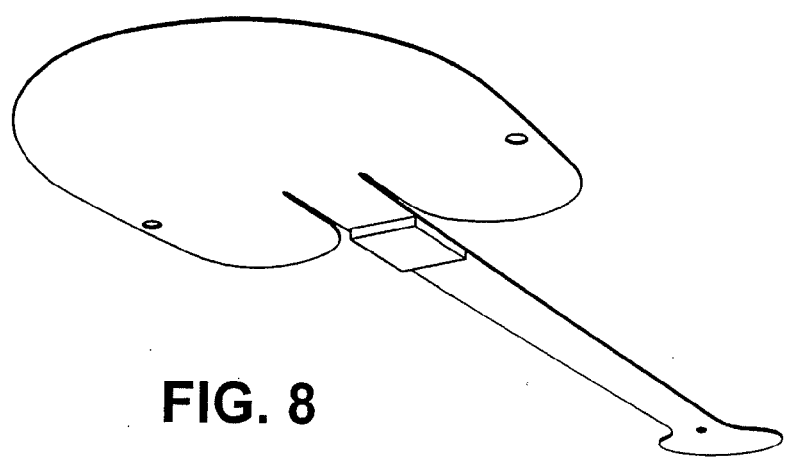
FIG. 8 illustrates an underside view of a prosthesis device including an RF coil with leaves/rabbit ears.
Figure 9:
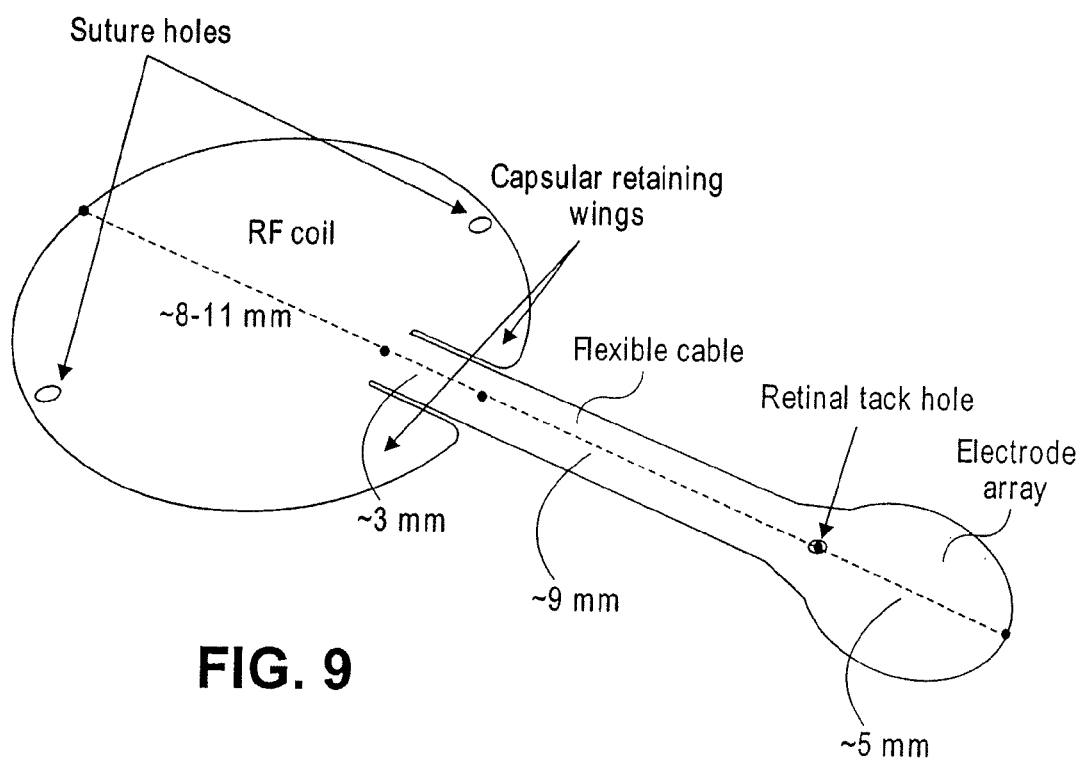
FIG. 9 illustrates a prosthesis device including an RF coil region with "anchor" shaped retention elements.
Figure 15:
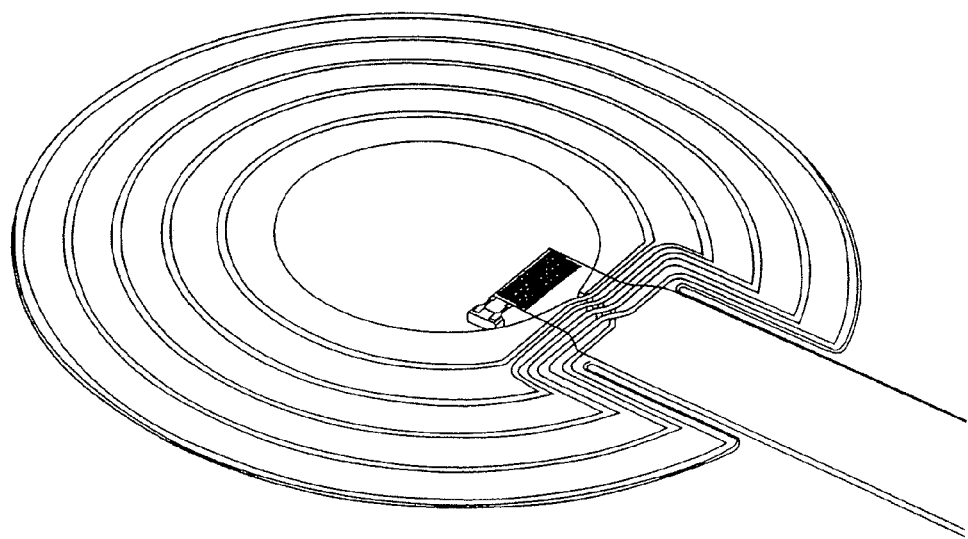
FIG. 15 illustrates an RF coil arrangement according to one embodiment. As shown, a chip, or circuit arrangement is located within the RF coil region.

According to one embodiment, the RF coil region includes a one or more retention elements to facilitate mechanical retention of the RF coil region within the capsular bag or anterior to it as shown in FIGS. 6-9. Examples of retention elements are the "rabbit ear" shaped elements as depicted in FIG. 6, and the "anchor" shaped elements of FIG. 9, in which the RF coil is situated in the continuous polymer region to the left of the dotted line. This morphology includes regions ("ears") protruding beyond the location at which the cable attaches to the RF coil region (and not directly attached to the cable). The retention elements are able to maintain the integrity of the capsule and retain the RF coil and capsular regions within the capsule even though the cable may bend (and thus exert a pulling force) when exiting this region. Thus, the advantage of the retention elements is the resistance force they provide when the device is implanted; the bending and threading of the electrode array and cable regions through the posterior capsule would not, by traction and the connection of the cable with the RF coil region, pull the coil into the vitreous cavity as well because they are not directly connected to this cable but are instead connected through the bulk of this region depicted on the left. As shown in FIG. 15, for example, a chip could reside within the RF coil region (thus within the capsule or anterior to it), at the point of attachment of the cable, or could, as depicted in FIG. 6, be situated along the cable region within the vitreous cavity. The precise geometry and morphology of the RF coil with retention elements can be varied, and the suture holes depicted are optionally provided to facilitate securing the device during implantation. Additionally, other mechanisms of attachment or further fastening of the device within the capsule can be employed.

In one embodiment, the subsystems and components of a prosthesis device 10 are all fabricated together during the same monolithic production process or run. An example of a process for fabricating an integrated device 10 according to one embodiment follows. In one aspect, a sacrificial layer of photoresist is first formed on a substrate as a release layer. The substrate can include any of a variety of materials such as silicon, glass, quartz, etc. A polymer such as parylene is then deposited, and conductive lines are then patterned on the polymer, e.g., using conventional masking techniques. In one aspect, a patterned layer of conductive material is formed to define one or more of the various subsystem components such as the RF coils, the chip elements, the interconnection cable lines and/or the electrodes. Conductive lines are formed by depositing a metal, a conductive polymer or other conductive material. The conductive material can be deposited by evaporation, sputtering, or electroplating, for example. In preferred aspects, the conductive material includes a metal material. Useful metals include titanium, platinum, platinum grey, platinum black, chromium, gold, iridium oxide, and others. In other aspects, the conductive material includes any electrically conducting medium such as a conducting polymer, a doped semiconductor material, graphite, or a combination of these conductive materials. One useful conductive polymer is carbonized parylene. Parylene can be carbonized either by exposing it in a hot furnace (preferably unoxygenated gas like nitrogenous gas) or by ion bombardment/implantation of parylene with carbon atoms. In the latter case, a mask can be used to mask off those areas that should not be carbonized (e.g., using a stencil, photoresist, metal, or other masking means). It should be appreciated that one or more different conductive materials can be used for different circuit elements, and that the various circuit elements can be formed of different materials. For example, the conductive lines in the cable region can be formed of carbonized parylene, the electrodes formed of a second material and the RF coil and chip elements formed of the same or different conductive material(s).

Another layer of polymer material (e.g. parylene) is then deposited to seal the conductive material. Any regions requiring exposure for electrical contact to the retina (e.g., electrodes in the retinal stimulation subsystem) or elements in other region are then opened (e.g., by oxygen plasma etching, excimer laser ablation, etc.). It should be appreciated that multiple conductive line patterning and polymer deposition steps may occur as needed, e.g., to define components and circuits for the power and data management subsystem 30. For example, U.S. patent application Ser. No. 11/130,814, titled "PARYLENE-BASED FLEXIBLE MULTI-ELECTRODE ARRAYS FOR NEURONAL STIMULATION AND RECORDING AND METHODS FOR MANUFACTURING THE SAME," filed May 16, 2005, and which is hereby incorporated by reference in its entirety, discloses examples of devices including multiple conductive layers and multiple parylene layers and methods for fabricating such devices.

The precise geometry of the device 10 can then be defined by masking off the device region by photoresist or some other method and etching the polymer surrounding the device away (or using other methods to cut or etch). The photoresist release layer can then be removed, separating the device from the substrate. In this manner, a single prosthesis device, including all of the components or subsystems, can be fabricated simultaneously in the same run, for instance, using standard microfabrication techniques. Additionally, multiple devices can be fabricated simultaneously in a batch fabrication process. For example, multiple devices can be formed simultaneously on a wafer. It should be appreciated that the precise geometries/morphologies of the device can be varied to accommodate different eyes, shapes, and surgical procedures/considerations.

It should be appreciated that devices according to the present invention are not restricted to one layer of conductive material. For example, it may be advantageous to provide a device with several alternative levels of conductors or electrodes. If, for instance, it is desirable to restrict a cable to a certain dimension (e.g., width) but keep the lines relatively large, one line can be run out to an electrode, covered entirely, then the next line and electrode layed down, the whole structure covered in polymer, and then all the electrodes opened up. One of the electrodes would be recessed by the thickness of the polymer covering the first line and electrode. Alternately, the electrode on the first layer can be formed at the same time as the overlying line and electrode, provided the underlying trace is first opened up, e.g., using RIE or laser ablation of the polymer layer.

Electrode Array

As discussed above, an electrode pattern can be formed on a polymer layer such as parylene, e.g., by masking, exposing and developing a photoresist layer as is well know. The electrode pattern is transferred to the parylene layer overlaying the conducting material to expose the underlying conductive material according to the desired electrode pattern. In certain aspects, the electrode pattern is transferred by a plasma etch such as a reactive ion etch (RIE). In general useful methods for transferring the pattern to the parylene (e.g., removing parylene) include plasma etching, laser ablation, blade cutting, melting, or any combination of these processes. The preferred masking material is photoresist, however other useful materials include polymers, metals, or a shadow mask (e.g., a stencil).

According to one embodiment, an electrode pattern includes an electrode spacing arranged to more closely match the receptors of target cells. Target cells matched may include photoreceptors, amacrine, horizontal, bipolar, or ganglion cells, for example. For example, in one embodiment, the electrode spacing is varied so as to more closely match the ganglion cell density in the retina. In certain aspects, the exposed electrodes are arranged in a pattern that is irregular or variable and not in a grid-like arrangement so as to better match the target. Because it is thought that electrical stimulation actually stimulates the ganglion cells, it is advantageous for the electrode layout to match that of the ganglion cells. Such a biomimetic electrode layout may lead to better function for patients by matching the natural visual density of the ganglion cells. If the target cells were the amacrine or bipolar cells, then, the electrode array layout could match those target cell densities instead. Here, such cell density matching is defined as "retinotopic" matching.

Figure 10:
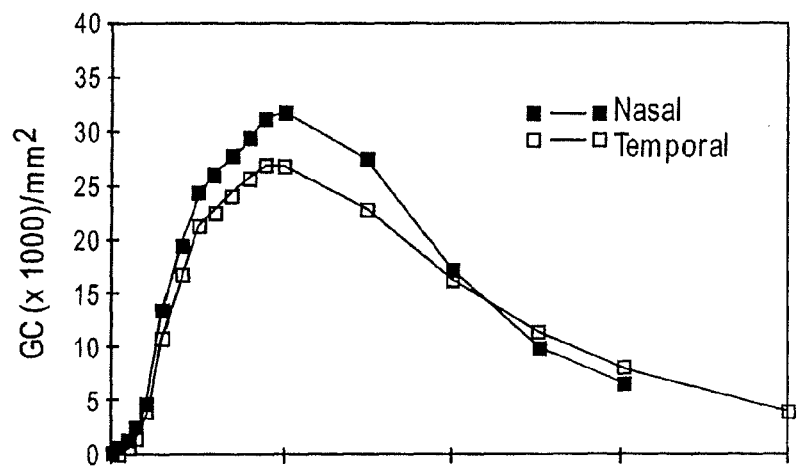
FIG. 10 is a graph showing ganglion cell densities in the retina as a function of radial position.
Figure 11:
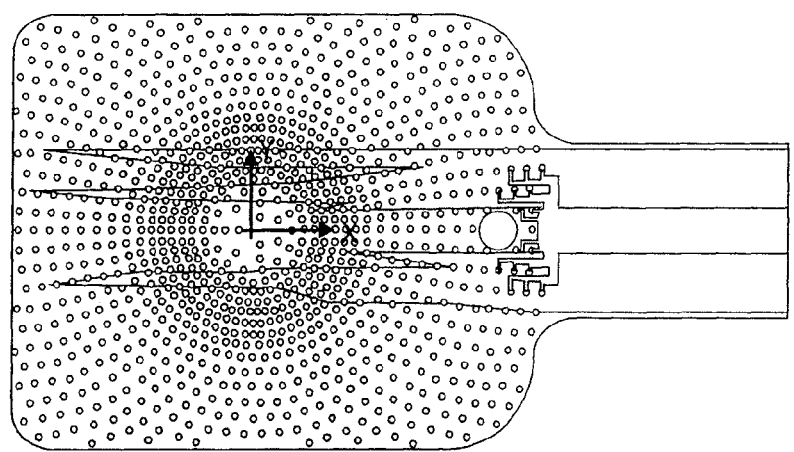
FIG. 11 shows an example of a "retinotopic" electrode array layout according to one embodiment.
Figure 12:
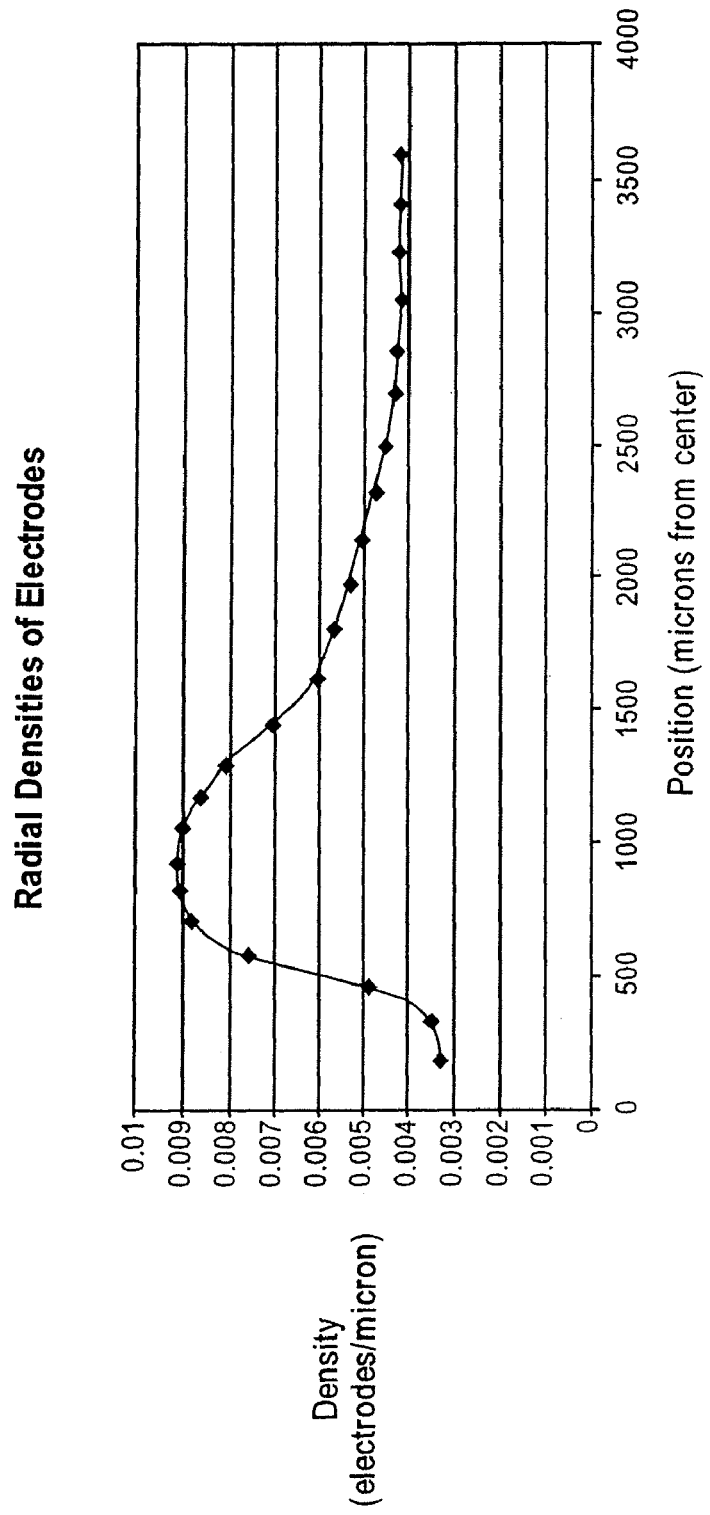
FIG. 12 is a graph showing approximate radial densities of electrodes in a pattern that more closely matches the density pattern of ganglion cells as shown in FIG. 10.

The ganglion cell density measured in human retinas is shown in FIG. 10. See, C. A. Curcio and K. A. Allen, "Topography of Ganglion-Cells in Human Retina," Journal of Comparative Neurology, vol. 300, pp. 5-25, 1990. An electrode array designed so that the electrode densities more closely match these ganglion cell densities is shown in FIG. 11. FIG. 12 shows the approximate radial densities of the electrode designed to match those in FIG. 10. However, it is important to note that these are not the exact dimensions and spacings required to match these target cell densities. In fact, based on the number of electrodes in the array as well as other considerations, these dimensions and spacings can be changed. It should be appreciated that the electrode pattern dimensions and distances may be varied based on electrode size, number, overall array geometry, target cells matched, or other considerations.

Figure 13:
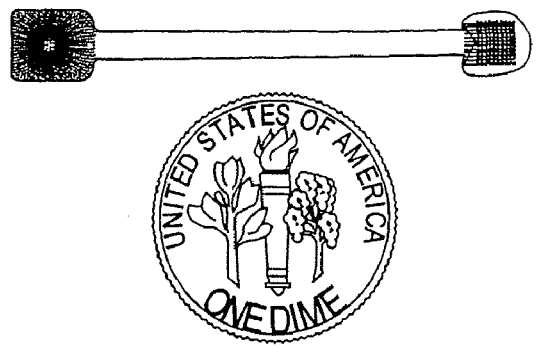
FIG. 13 illustrates an example of a fabricated device with a retinotopic array layout according to one embodiment.
Figure 14:
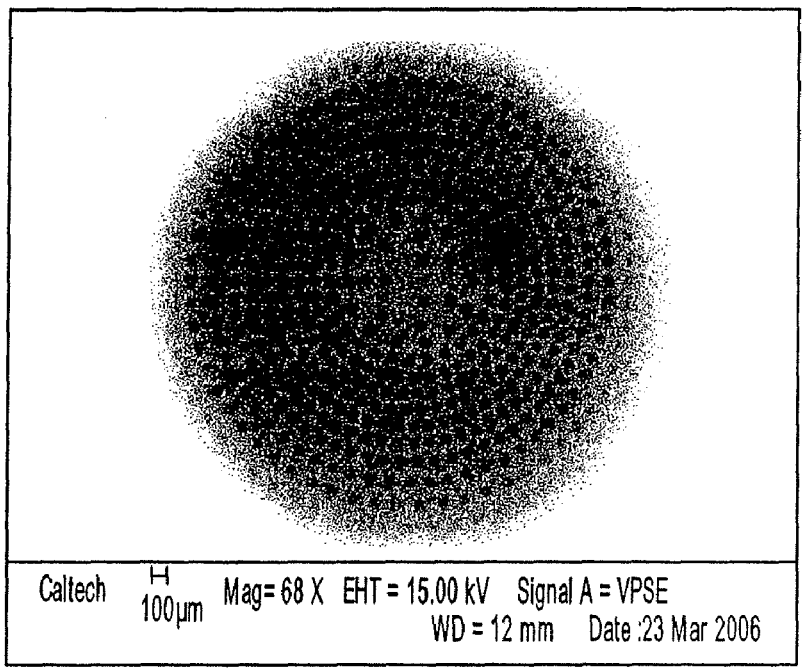
FIG. 14 is an SEM image of a fabricated electrode array according to one embodiment.

A fabricated retinotopic electrode array is shown in FIG. 13. FIG. 14 shows a scanning electron micrograph of the electrode array region of one of these fabricated electrode arrays.

Implantation Example

Figure 16:
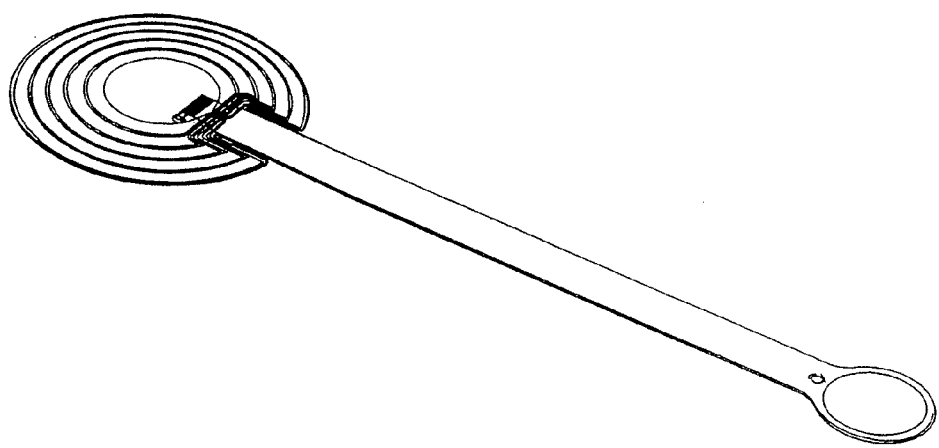
FIG. 16 illustrates a prosthesis device including the arrangement of FIG. 15 according to one embodiment.
Figure 17:
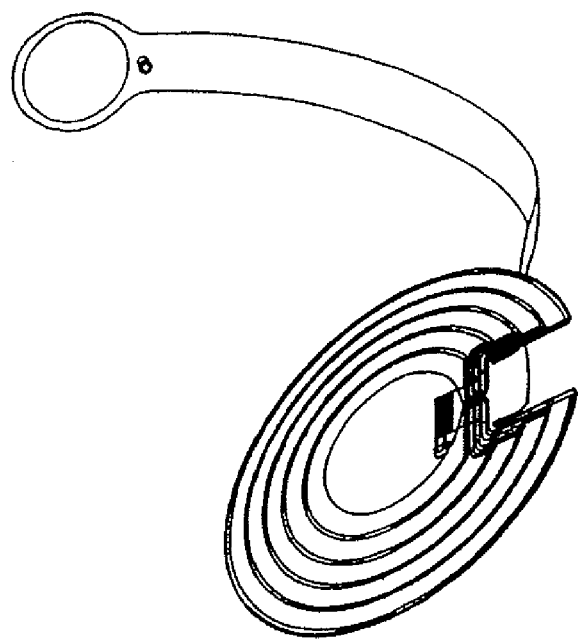
FIG. 17 illustrates the prosthesis device of FIG. 16 rolled up to match the topology of the eye.
Figure 18:
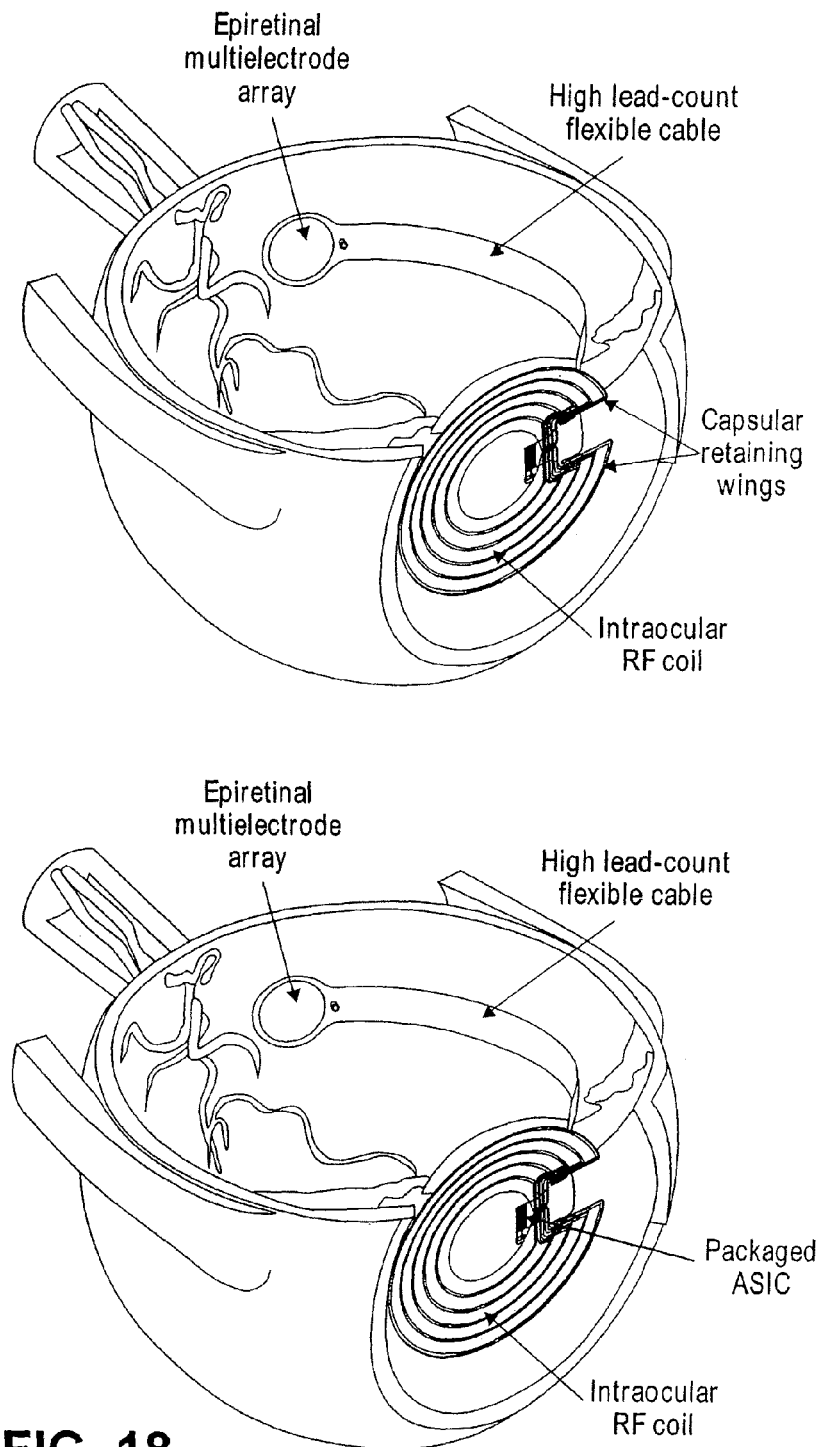
FIGS. 18-20 illustrate different views of the positioning and layout of the device of FIG. 16 when implanted in an eye.
Figure 19:
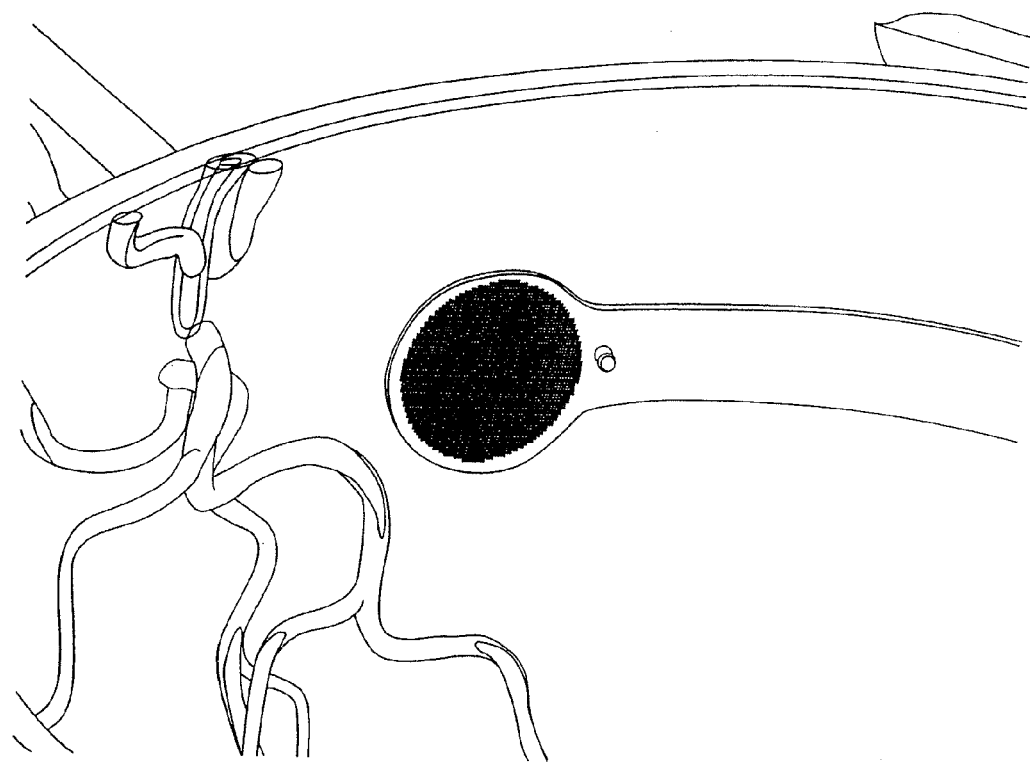
Figure 20:
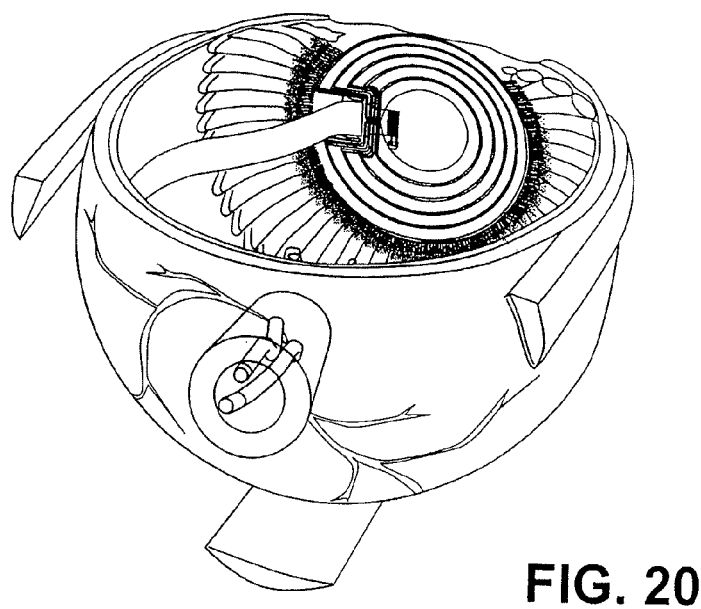

FIG. 16 shows an example of an integrated prosthesis device according to one embodiment. FIGS. 17-20 illustrate examples of use of the prosthesis device according to one embodiment. A shown in FIG. 17, the prosthesis device of FIG. 16 can be rolled up to match the topology of the eye. FIGS. 18-20 illustrate the positioning and layout of the device when implanted in an eye.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of fabricating an integrated intraocular retinal prosthesis device having an electrode array region, a power and data management region and a cable region connecting the electrode region with the power and data management region, the method comprising:

forming a patterned layer of conductive material on a first layer of polymer material, said patterned conductive layer defining circuit elements of the power and data management region, the electrode region and the cable region wherein the circuit elements of the power and data management region include one or more RF coil elements formed of the conductive material;

covering the patterned conductive layer with a second polymer layer; and removing a portion of the second polymer layer in the electrode array region so as to expose at least a portion of the patterned conductive layer to form an exposed electrode array.

2. The method of claim 1, wherein the conductive material comprises carbonized parylene.

3. The method of claim 1, wherein the conductive material comprises a conductive metal selected from the group consisting of gold, platinum, chromium, titanium, platinum and iridium oxide.

4. The method of claim 1, wherein the first polymer layer and the second polymer layer each comprise one or more of parylene A, parylene C, parylene AM, parylene F, parylene N, parylene HT or parylene D.

5. The method of claim 1, wherein the device includes one or more retention elements configured to retain the RF coil elements in an implant region of an eye.

6. The method of claim 1, wherein forming the patterned conductive layer comprises:

depositing a layer of photoresist on the polymer layer;

patterning the photoresist with a mask;

removing the patterned photoresist to expose the polymer layer;

depositing the conductive material on the exposed polymer layer; and removing the remaining photoresist.

7. The method of claim 6, wherein depositing the conductive material includes one of an e-beam evaporation process, a sputtering process or an electroplating process.

8. The method of claim 1, further comprising:

depositing a layer of photoresist on a substrate; and forming the first layer of polymer material on the photoresist.

9. The method of claim 8, wherein the substrate comprises a material selected from the group consisting of silicon, glass, and quartz.

10. The method of claim 9, further comprising removing the photoresist layer so as to separate the device from the substrate.

11. The method of claim 1, wherein the cable region includes one or more conductive lines formed of the conductive material, said lines coupling the electrode array with one or more circuit elements in the power and data management region.

12. The method of claim 1, wherein the circuit elements of the power and data management region include one of a chip or a circuit arrangement configured to provide control signals to the electrode array.

13. The method of claim 1, wherein the exposed electrode array includes electrodes arranged in a pattern that mimics the density pattern of ganglion cells in a retina.

14. The method of claim 1, wherein the exposed electrode array includes electrodes arranged in a pattern having an irregular density.

15. The method of claim 1, wherein removing a portion of the second polymer layer comprises:

depositing a layer of photoresist on the second polymer layer;

patterning the photoresist with a mask;

removing the patterned photoresist to expose portions of the second polymer layer; and etching the exposed portions of the second polymer layer.

16. A method of fabricating an integrated intraocular retinal prosthesis device having an electrode array region, a power and data management region and a cable region connecting the electrode region with the power and data management region, the method comprising:

forming a patterned layer of conductive material on a first layer of polymer material, said patterned conductive layer defining circuit elements of the power and data management region, the electrode region and the cable region, wherein the cable region includes one or more conductive lines formed of the conductive material, said lines coupling the electrode array with one or more circuit elements in the power and data management region;

covering the patterned conductive layer with a second polymer layer; and removing a portion of the second polymer layer in the electrode array region so as to expose at least a portion of the patterned conductive layer to form an exposed electrode array.

* * * * *